United States Patent
Hares et al.

(10) Patent No.: US 10,299,873 B2
(45) Date of Patent: May 28, 2019

(54) SURGICAL INSTRUMENT DRIVING MECHANISM

(71) Applicant: CMR SURGICAL LIMITED, Cambridge (GB)

(72) Inventors: Luke David Ronald Hares, Cambridge (GB); Keith Marshall, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 414 days.

(21) Appl. No.: 15/161,345

(22) Filed: May 23, 2016

(65) Prior Publication Data
US 2016/0338788 A1 Nov. 24, 2016

(30) Foreign Application Priority Data

May 22, 2015 (GB) .................................. 1508807.3
May 19, 2016 (GB) .................................. 1608816.3

(51) Int. Cl.
*A61B 34/00* (2016.01)
*A61B 34/30* (2016.01)

(52) U.S. Cl.
CPC .............. *A61B 34/71* (2016.02); *A61B 34/30* (2016.02); *A61B 2034/715* (2016.02)

(58) Field of Classification Search
CPC ................................ A61B 34/71; A61B 34/30
See application file for complete search history.

(56) References Cited

U.S. PATENT DOCUMENTS

| 10,005,181 B2* | 6/2018 | Hasegawa | B25J 9/1612 |
| 2003/0100892 A1* | 5/2003 | Morley | A61B 17/062 |
| | | | 606/1 |
| 2012/0330287 A1 | 12/2012 | Yim | |
| 2018/0147017 A1* | 5/2018 | Marshall | A61B 34/71 |

OTHER PUBLICATIONS

United Kingdom Search Report from corresponding United Kingdom Application No. GB1508807.3 dated Dec. 4, 2015.

* cited by examiner

*Primary Examiner* — Terence Boes
(74) *Attorney, Agent, or Firm* — Lando & Anastasi, LLP (57) ABSTRACT

A robotic surgical instrument comprising a shaft, an articulation attached to the distal end of the shaft, and a driving mechanism at the proximal end of the shaft. The articulation comprises a plurality of joints for articulating an end effector, the plurality of joints driveable by at least first and second pairs of driving elements. The driving mechanism comprises a pulley arrangement and a pulley drive. The pulley arrangement comprises first and second pulleys attached together such that their separation is fixed, wherein the first pair of driving elements is constrained to move around the first pulley, and the second pair of driving elements is constrained to move around the second pulley. The pulley drive is configured to linearly displace the pulley arrangement, such that a linear displacement in one direction away from the distal end of the shaft causes the first pair of driving elements to be tensioned and the second pair of driving elements to be de-tensioned, and a linear displacement in an opposing direction towards the distal end of the shaft causes the second pair of driving elements to be tensioned and the first pair of driving elements to be de-tensioned.

18 Claims, 4 Drawing Sheets

SURGICAL INSTRUMENT DRIVING MECHANISM

CROSS-REFERENCE TO RELATED APPLICATION

This application claims the benefit under 35 U.S.C. § 119 of United Kingdom Patent Application No. 1508807.3 filed on May 22, 2015 which is hereby incorporated herein by reference in its entirety for all purposes, and this application also claims the benefit under 35 U.S.C. § 119 of United Kingdom Patent Application No. 1608816.3 filed on May 19, 2016.

BACKGROUND

It is known to use robots for assisting and performing surgery. Surgical robots normally consist of a base, an arm, and an instrument. The base supports the robot, and is itself attached rigidly to, for example, the operating theatre floor, the operating theatre ceiling or a trolley. The arm extends between the base and the instrument. The arm typically has a plurality of articulations, which are used to locate the surgical instrument in a desired location relative to the patient. The surgical instrument is attached to the distal end of the robot arm. The surgical instrument penetrates the body of the patient at a port so as to access the surgical site.

Figure 1:
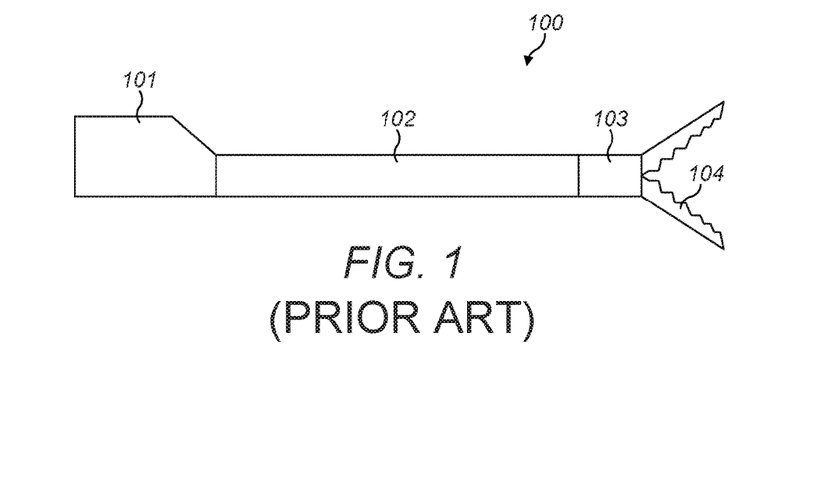
FIG. 1 illustrates a known surgical instrument.

FIG. 1 illustrates a typical surgical instrument 100 for performing robotic laparoscopic surgery. The surgical instrument comprises a base 101 by which the surgical instrument connects to the robot arm. A shaft 102 extends between base 101 and articulation 103. Articulation 103 terminates in an end effector 104. In FIG. 1, a pair of serrated jaws are illustrated as the end effector 104. The articulation 103 permits the end effector 104 to move relative to the shaft 102. It is desirable for at least two degrees of freedom to be provided to the motion of the end effector 104 by means of the articulation.

Figure 2:
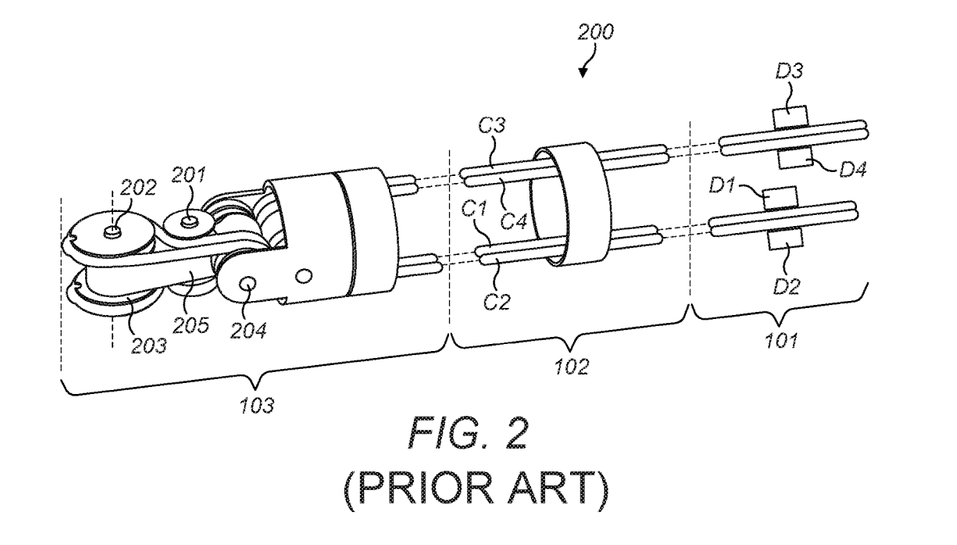
FIG. 2 illustrates a known cabling arrangement of a surgical instrument.

FIG. 2 illustrates an example of a known cabling arrangement 200 in a surgical instrument for transferring drive from the base of the surgical instrument 101 through the shaft 102 to the articulation 103. Cable pair C1, C2 terminate in the articulation as a loop around capstan 202. They then pass as a pair around one side of capstan 201. From there, the cable pair C1, C2 passes over capstan 204 and down through shaft 102 to the base of the instrument 101. Cable pair C3, C4 terminate in the articulation as a loop around capstan 203. They then pass as a pair around the other side of capstan 201 to C1, C2. From there, the cable pair C3, C4 passes under capstan 204 and down through shaft 102 to the base of the instrument 101.

Rotation of yoke 205 about capstan 204 causes the articulation 103 and hence the end effector 104 to pitch about the capstan 204. Pitching in one direction is enabled by pulling cable pair C1, C2 and releasing cable pair C3, C4. Pitching in the other direction is enabled by pulling cable pair C3, C4 and releasing cable pair C1, C2. Rotation of capstan 202 causes one jaw of end effector 104 to move. Movement in one direction is enabled by pulling cable C1 and releasing cable C2. Movement in the other direction is enabled by pulling cable C2 and releasing cable C1. Rotation of capstan 203 causes the other jaw of end effector 104 to move. Movement in one direction is enabled by pulling cable C3 and releasing cable C4. Movement in the other direction is enabled by pulling cable C4 and releasing cable C3. Cables C1, C2, C3 and C4 are driven individually and independently by drivers D1, D2, D3 and D4 respectively.

In the context of minimally invasive surgery, it is desirable to reduce the external diameter of the shaft in order to minimise the size of the incision through the skin of the patient and disruption inside the patient's body. It is also desirable to minimise the weight of the surgical instrument so as to minimise the size and weight of the robot base and arm required to support the instrument, thereby enabling the robot as a whole to be more moveable within the operating theatre.

It would therefore be desirable to reduce the size and weight of the driving mechanism in the surgical instrument whilst retaining the ability to articulate the end effector as described above.

SUMMARY OF THE INVENTION

According to an aspect of the invention, there is provided A robotic surgical instrument comprising: a shaft; an articulation attached to the distal end of the shaft, the articulation comprising a plurality of joints for articulating an end effector, the plurality of joints driveable by at least first and second pairs of driving elements; and a driving mechanism at the proximal end of the shaft, the driving mechanism comprising: a pulley arrangement comprising first and second pulleys attached together such that their separation is fixed, wherein the first pair of driving elements is constrained to move around the first pulley, and the second pair of driving elements is constrained to move around the second pulley; and a pulley drive configured to displace the pulley arrangement, such that a displacement in one direction causes the first pair of driving elements to be tensioned and the second pair of driving elements to be de-tensioned, and a displacement in an opposing direction causes the second pair of driving elements to be tensioned and the first pair of driving elements to be de-tensioned.

Suitably, the pulley drive is configured to displace the pulley arrangement such that a displacement in one direction causes the first pair of driving elements to be tensioned and the second pair of driving elements to be compressed, and a displacement in an opposing direction causes the second pair of driving elements to be tensioned and the first pair of driving elements to be compressed.

Suitably, the articulation is a wrist articulation and one of the plurality of joints is a pitch joint configured to pitch the wrist articulation, the first and second pairs of driving elements being connected to the wrist articulation such that when the pulley drive displaces the pulley arrangement in one direction the wrist articulation pitches in one direction about the pitch joint, and when the pulley drive displaces the pulley arrangement in the opposing direction the wrist articulation pitches in an opposing direction about the pitch joint.

The pulley drive may be configured to displace the pulley arrangement in a direction parallel to the longitudinal axis of the shaft.

Suitably, at the proximal end of the shaft, the first pair of driving elements is constrained to move around the first pulley only with no further intervening pulleys, such that when the pulley drive displaces the pulley arrangement away from the distal end of the shaft, the first pair of driving elements is tensioned.

Suitably, the second pair of driving elements is further constrained to move around third and fourth pulleys, the third and fourth pulleys being located further from the articulation than the pulley arrangement, wherein the second pair of driving elements extends from the articulation through the shaft, around the third and fourth pulleys to the second pulley, such that when the pulley drive displaces the pulley arrangement towards the distal end of the shaft, the second pair of driving elements is tensioned.

Suitably, the driving mechanism further comprises a first drive configured to drive the first pair of driving elements, such that a drive applied in one direction causes a first one of the first pair of driving elements to be tensioned and a second one of the first pair of driving elements to be compressed, and a drive applied in an opposing direction causes the first one of the first pair of driving elements to be compressed and the second one of the first pair of driving elements to be tensioned.

The first one of the plurality of joints may be configured to actuate opposing first and second jaws of an end effector, the first pair of driving elements being connected to the articulation such that when the first drive applies a drive in one direction the first jaw rotates in one direction about that joint, and when the first drive applies a drive in an opposing direction the first jaw rotates in an opposing direction about that joint.

Suitably, the first drive is a linear drive.

The driving mechanism may further comprise a second drive configured to drive the second pair of driving elements, such that a drive applied in one direction causes a first one of the second pair of driving elements to be tensioned and a second one of the second pair of driving elements to be compressed, and a drive applied in an opposing direction causes the first one of the second pair of driving elements to be compressed and the second one of the second pair of driving elements to be tensioned.

One of the plurality of joints may be configured to actuate opposing first and second jaws of an end effector, the second pair of driving elements being connected to the articulation such that when the second drive applies a drive in one direction the second jaw rotates in one direction about that joint, and when the second drive applies a drive in an opposing direction the second jaw rotates in an opposing direction about that joint.

The second drive is a linear drive.

The driving elements may be elongate and flexible. The driving elements may be cables. The driving elements may resist compression and tension forces. Each pair of driving elements may be formed of opposed portions of a single elongate element secured to one of the plurality of joints of the articulation. Each driving element of the first pair of driving elements may be formed of a distinct elongate element secured to one of the plurality of joints of the articulation and secured to the first pulley. Each driving element of the second pair of driving elements may be formed of a distinct elongate element secured to one of the plurality of joints of the articulation and secured to the second pulley.

BRIEF DESCRIPTION OF THE FIGURES

The present invention will now be described by way of example with reference to the accompanying drawings. In the drawings.

DETAILED DESCRIPTION

Figure 3:
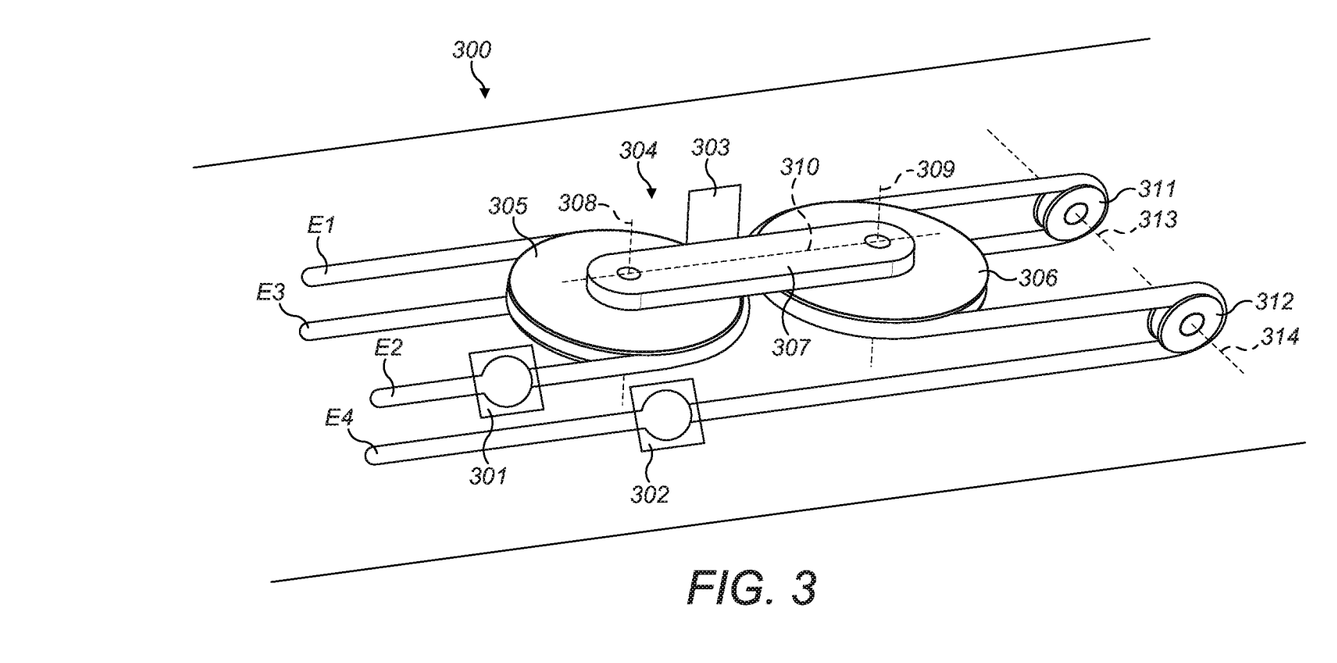
FIG. 3 illustrates a driving mechanism at the end of the surgical instrument distal from the end effector.

FIG. 3 illustrates a schematic drawing of an exemplary driving mechanism 300 of the interior of a robotic surgical instrument at the end of the surgical instrument distal from the end effector. The surgical instrument as a whole has the general form shown in FIG. 1. In other words, the surgical instrument comprises a base 101 by which the surgical instrument connects to the surgical robot arm. The instrument base is designed cooperatively with the terminal end of the surgical robot arm, such that the instrument base is releasably attachable to the terminal end of the robot arm. A shaft 102 extends between the base 101 and an articulation 103. The articulation 103 is connected at its proximal end to the shaft 102 and at its distal end to an attachment suitable for attaching an end effector 104. The shaft 102 and articulation 103 are all hollow. This allows passage of elements up these sections to actuate the end effector 104. It also reduces the weight of the surgical instrument.

The end effector may take any suitable form. For example, the end effector may be smooth jaws, serrated jaws, a gripper, a pair of shears, a needle for suturing, a camera, a laser, a knife, a stapler, a cauteriser, a suctioner.

The driving mechanism of FIG. 3 is arranged to drive two pairs of driving elements, E1, E2 and E3, E4. The driving elements may, for example, be cables. The driving mechanism of FIG. 3 enables the four driving elements E1, E2, E3 and E4 to be driven using only three drives, 301, 302, 303.

The driving mechanism of FIG. 3 comprises a pulley arrangement 304 which couples together the two pairs of driving elements E1, E2 and E3, E4. Pulley arrangement 304 comprises two pulleys 305 and 306 connected by arm 307. Arm 307 connects pulleys 305 and 306 together such that their separation is fixed. Arm 307 is rigid. The pulleys 305 and 306 are rotatably mounted to the arm. Each of the pulleys 305 and 306 rotates relative to the arm 307 independently of the other pulley 305 or 306. In the example shown in FIG. 3, the pulleys 305 and 306 are arranged parallel to each other in the same plane. Each pulley has two opposing circular faces separated by a grooved edge for receiving the driving elements. The pulleys are arranged such that their circular profiles are in the same plane. The pulleys 305 and 306 are edge on. The facing surfaces of the pulleys are their grooved edges. The centre of pulley 305 is rotatably mounted to the arm 307 such that pulley 305 rotates about an axis 308 which is perpendicular to the circular faces of the pulley 305. The only permitted motion of pulley 305 relative to the arm 307 is rotation about axis 308. The centre of pulley 306 is rotatably mounted to the arm 307 such that pulley 306 rotates about an axis 309 which is perpendicular to the circular faces of the pulley 306. The only permitted motion of pulley 306 relative to the arm 307 is rotation about axis 309. Axes 308 and 309 are parallel to each other. The pulley arrangement is arranged longitudinally in the shaft. In other words, the longitudinal axis of the pulley arrangement is parallel to the longitudinal axis of shaft 102. The longitudinal axis of pulley arrangement 304 is the axis which connects the centre of pulley 305 with the centre of pulley 306.

Driving elements pair E1, E2 engage pulley 305 of pulley arrangement 304. Pulley 305 receives driving elements E1, E2 from shaft 102. Driving elements E1, E2 are seated in the grooved edge of pulley 305. This constrains driving element pair E1, E2 to move around the pulley. As viewed from the articulation end of the shaft, driving element pair E1, E2 is wound around the far side of pulley 305. In FIG. 3, driving elements E1, E2 are formed of opposed portions of a single elongate element. This single elongate element loops around the pulley 305. In the arrangement of FIG. 3, the only element which driving element pair E1, E2 engages with which causes the direction of driving elements E1, E2 to change is pulley 305. In other words, driving element pair E1, E2 does not engage with any further pulleys or other elements at the proximal end of the shaft which cause the direction of driving elements E1, E2 to change. Suitably, driving element pair E1, E2 engages solely with pulley 305 in the proximal end of the shaft. Suitably, driving element pair E1, E2 does not engage with any other pulleys in the proximal end of the shaft.

Driving elements pair E3, E4 engage pulley 306 of pulley arrangement 304. Pulley 306 receives driving elements E3, E4 from shaft 102. As the driving element E3 extends from the articulation 103 through the shaft 102, it first reaches pulley 311. Pulley 311 is located at the proximal end of the shaft further from the articulation than the pulley arrangement 304. Thus, driving element E3 extends through the shaft from the articulation beyond the pulley arrangement 304 to pulley 311. Pulley 311 is mounted transverse to pulley arrangement 304. The axis 313 about which pulley 311 rotates is perpendicular to the axis 309 about which pulley 306 rotates. Driving element E3 is seated in the grooved edge of pulley 311. This constrains driving element E3 to move around pulley 311. Pulley 311 causes the direction of driving element E3 to change by 180°. Driving element E3 approaches pulley 311 from the articulation 103 in a direction parallel to the longitudinal direction of the shaft.

After engaging with pulley 311, driving element leaves pulley 311 in a direction parallel to the longitudinal direction of the shaft towards the articulation 103. Driving element E3 leaves pulley 311 and engages with pulley 306 of pulley arrangement 304.

As the driving element E4 extends from the articulation 103 through the shaft 102, it first reaches pulley 312. Pulley 312 is located at the proximal end of the shaft further from the articulation than the pulley arrangement 304. Thus, driving element E4 extends through the shaft from the articulation beyond the pulley arrangement 304 to pulley 312. Pulley 312 is mounted transverse to pulley arrangement 304. The axis 314 about which pulley 312 rotates is perpendicular to the axis 309 about which pulley 306 rotates. Pulley 312 is mounted parallel to pulley 311. Circular faces of pulleys 311 and 312 are facing each other. The axis 313 about which pulley 311 rotates and the axis 314 about which pulley 312 rotates are parallel. Suitably, axes 312 and 314 are collinear. Driving element E4 is seated in the grooved edge of pulley 312. This constrains driving element E4 to move around pulley 312. Pulley 312 causes the direction of driving element E4 to change by 180°. Driving element E4 approaches pulley 312 from the articulation 103 in a direction parallel to the longitudinal direction of the shaft. After engaging with pulley 312, driving element leaves pulley 312 in a direction parallel to the longitudinal direction of the shaft towards the articulation 103. Driving element E4 leaves pulley 312 and engages with pulley 306 of pulley arrangement 304.

Driving elements E3, E4 are seated in the grooved edge of pulley 306. This constrains driving element pair E3, E4 to move around the pulley. As viewed from the articulation end of the shaft: driving element E3 is wound around the far side of pulley 311; driving element E4 is wound around the far side of pulley 312; and driving element pair E3, E4 is wound around the near side of pulley 306. In FIG. 3, driving elements E3, E4 are formed of opposed portions of a single elongate element. This single elongate element loops around the pulley 306. In the arrangement of FIG. 3, the only elements which driving element pair E1, E2 engage with which causes the direction of driving elements E1, E2 to change are pulleys 311, 312 and 306. In other words, driving element pair E3, E4 does not engage with any further pulleys or other elements at the proximal end of the shaft which cause the direction of driving elements E3, E4 to change. Suitably, driving element pair E3, E4 engages solely with pulleys 311, 312 and 306 in the proximal end of the shaft. Suitably, driving element pair E3, E4 does not engage with any other pulleys in the proximal end of the shaft.

The driving mechanism illustrated in FIG. 3 comprises three drives: 301, 302 and 303. First drive 301 is connected to driving element pair E1, E2. First drive 301 may be connected to driving element pair E1, E2 anywhere along the section of driving element pair E1, E2 which is in the proximal end of the shaft 102. First drive 301 drives the driving element pair E1, E2 such that when driven in one direction E1 is tensioned and E2 is de-tensioned, and when driven in the other direction E2 is tensioned and E1 is de-tensioned. The de-tensioning may be releasing tension from the driving element. In other words, relaxing the driving element. However, suitably, the de-tensioning is a compression. In other words, the drive 301 both pulls one driving element and pushes the other driving element of the pair concurrently. First drive 301 may be any suitable drive which is capable of engaging with the driving element pair E1, E2 in this way. For example, first drive 301 may be a linear drive. This may be implemented using a motor and a lead screw arrangement.

Second drive 302 may be connected to driving element pair E3, E4 anywhere along the section of driving element pair E3, E4 which is in the proximal end of the shaft 102. Second drive 302 drives the driving element pair E3, E4 such that when driven in one direction E3 is tensioned and E4 is de-tensioned, and when driven in the other direction E4 is tensioned and E3 is de-tensioned. The de-tensioning may be releasing tension from the driving element. In other words, relaxing the driving element. However, suitably, the de-tensioning is a compression. In other words, the drive 302 both pulls one driving element and pushes the other driving element of the pair concurrently. Second drive 302 may be any suitable drive which is capable of engaging with the driving element pair E3, E4 in this way. For example, second drive 302 may be a linear drive. This may be implemented using a motor and a lead screw arrangement.

Pulley drive 303 is attached to pulley arrangement 304. Pulley drive 303 displaces pulley arrangement 304 as a whole. In other words, pulley drive 303 displaces pulley 305, pulley 306 and arm 307 as a unit. Pulley drive 303 couples the motion of driving element pair E1, E2 and driving element pair E3, E4. Pulley drive 303 displaces pulley arrangement 304 such that when driven in one direction driving element pair E1, E2 are tensioned and driving element pair E3, E4 are de-tensioned. Conversely, when pulley drive 303 displaces pulley arrangement 304 in the other direction driving element pair E3, E4 are tensioned and driving element pair E1, E2 are de-tensioned. The de-tensioning may be releasing tension from the driving element pair. In other words, relaxing the driving element pair. However, suitably, the de-tensioning is a compression. In other words, pulley drive 303 both pulls one driving element pair and pushes the other driving element pair concurrently. Pulley drive 303 suitably enables the described tensioning and de-tensioning of the driving element pairs by displacing the pulley arrangement 304 linearly. Suitably, this displacement is in a direction parallel to the axis 310 which connects the centres of pulleys 305 and 306. Suitably, the displacement is in a direction which is parallel to the longitudinal axis of the shaft 102. Pulley drive 303 may be any suitable drive which is capable of engaging with the driving element pairs E1, E2 and E3, E4 in this way. For example, pulley drive 303 may be a linear drive. This may be implemented using a motor and a lead screw arrangement.

Figure 4:
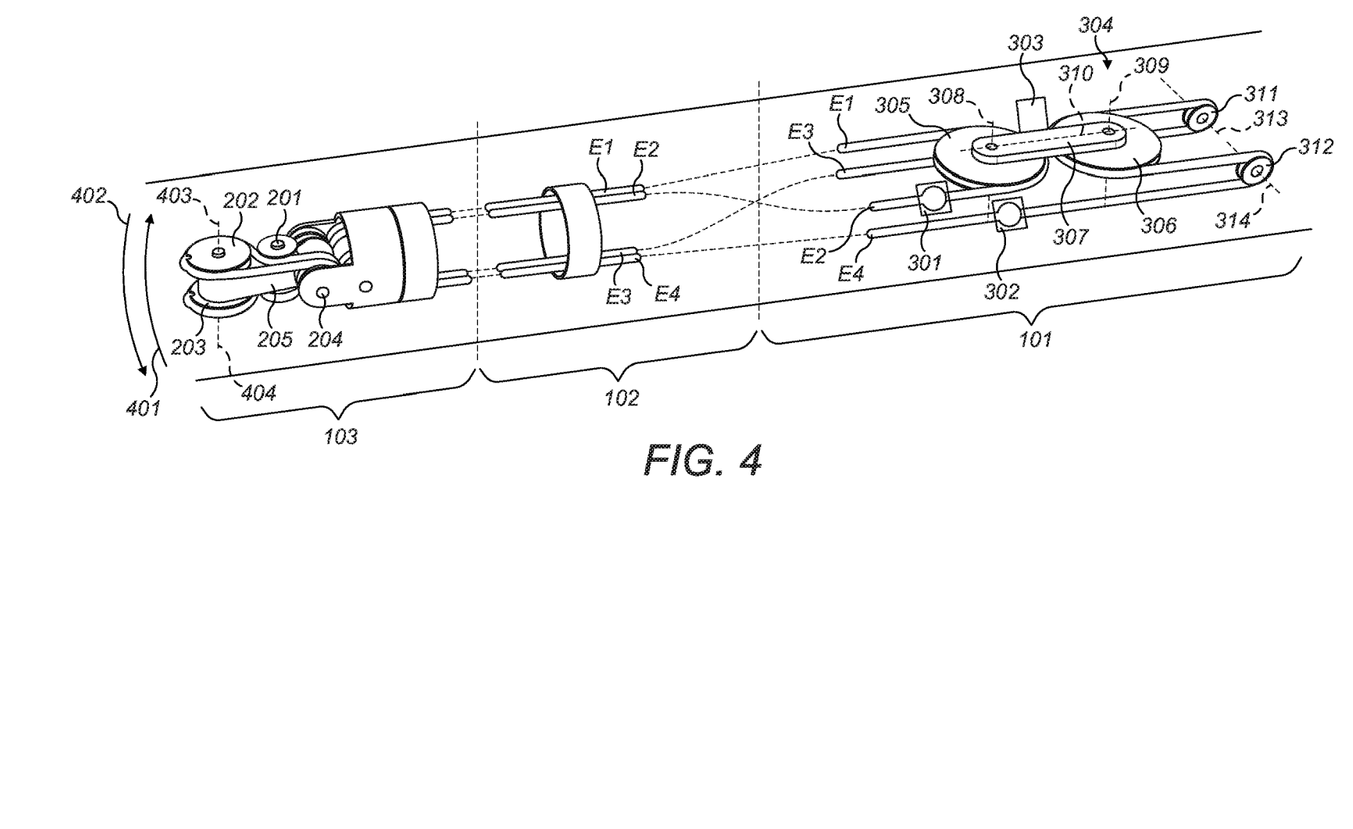
FIG. 4 illustrates the driving mechanism of FIG. 3 as applied in an articulated surgical instrument.

FIG. 4 illustrates a configuration in which the driving mechanism of FIG. 3 is used to drive an articulation 103 at the distal end of the instrument shaft 102. Articulation 103 is as described with reference to FIG. 2. The articulation comprises a plurality of joints for articulating an end effector. The end effector comprises two opposing jaws. One of these jaws is rigidly attached to capstan 202. The other jaw of the end effector is rigidly attached to capstan 203. The joints of the articulation 103 are driven by the driving element pairs E1, E2 and E3, E4 of FIG. 3. Driving element pairs E1, E2 and E3, E4 engage the driving mechanism 300 as described with reference to FIG. 3. Driving element pairs E1, E2, and E3, E4 extend through the hollow shaft 102 to the articulation 103 at the distal end of the shaft. Driving element pairs E1, E2 and E3, E4 engage with the articulation 103 at the distal end of the shaft as described with reference to FIG. 2, where E1 and E2 correspond to C3 and C4, and E3 and E4 correspond to C1 and C2.

The articulation is a wrist articulation, which includes pitch joint 204. Rotation about pitch joint 204 causes the wrist, and hence the end effector 104, to pitch relative to the shaft 102. Pitch joint 204 is caused to rotate in the direction marked 401 by tensioning driving element pair E3, E4 and de-tensioning or compressing driving element pair E1, E2. This is achieved by pulley drive 303 driving the pulley arrangement 304 so as to displace the pulley arrangement towards the articulation 301. Suitably, the pulley drive 303 linearly displaces the pulley arrangement 304 towards the distal end of the shaft. Conversely, pitch joint 204 is caused to rotate in the opposing direction marked 402 by tensioning driving element pair E1, E2 and de-tensioning or compressing driving element pair E3, E4. This is achieved by pulley drive 303 driving the pulley arrangement 304 so as to displace the pulley arrangement away from the articulation 301. Suitably, the pulley drive 303 linearly displaces the pulley arrangement 304 away from the distal end of the shaft.

Rotation about capstan 202 causes a first jaw of the end effector to rotate about the central axis 403 of capstan 202. The first jaw is caused to rotate in the direction marked 401 by tensioning driving element E3 and de-tensioning or compressing driving element E4. This is achieved by second drive 302 driving driving element pair E3, E4 in one direction. Conversely, the first jaw is caused to rotate in the opposing direction marked 402 by tensioning driving element E4 and de-tensioning or compressing driving element E3. This is achieved by second drive 302 driving driving element pair E3, E4 in an opposing direction to that discussed above. The tension status of driving elements E1 and E2 are immaterial to driving rotation of the first jaw about capstan 202. The motions of driving element pair E1, E2 and driving element pair E3, E4 are not coupled when driving rotation about capstan 202.

Rotation about capstan 203 causes a second jaw of the end effector to rotate about the central axis 404 of capstan 203. Central axis 404 of capstan 203 is parallel to central axis 403 of capstan 202. Suitably, central axis 404 of capstan 203 is collinear with central axis 403 of capstan 202. The second jaw is caused to rotate in the direction marked 401 by tensioning driving element E1 and de-tensioning or compressing driving element E2. This is achieved by first drive 301 driving driving element pair E1, E2 in one direction. Conversely, the second jaw is caused to rotate in the opposing direction marked 402 by tensioning driving element E2 and de-tensioning or compressing driving element E1. This is achieved by first drive 301 driving driving element pair E1, E2 in an opposing direction to that discussed above. The tension status of driving elements E3 and E4 are immaterial to driving rotation of the second jaw about capstan 203. The motions of driving element pair E1, E2 and driving element pair E3, E4 are not coupled when driving rotation about capstan 203.

The driving mechanism 300 independently drives motion of pitch joint 204 and each of the jaws by capstans 202 and 203. One or both jaws may be actuated concurrently with pitching the wrist by driving the driving elements E1, E2, E3 and E4 as described above.

The driving elements E1, E2, E3 and E4 are flexible. Each driving element is elongate. Each driving element can be flexed laterally to its main extent. In other words, each driving element can be flexed transversely to its longitudinal axis. Each driving element is not flexible along its main extent. Each driving element resists compression and tension forces acting in the direction of its longitudinal axis. Thus, the driving elements are able to transfer drive from the proximal end of the instrument to the articulation. The driving elements may be cables.

Each driving element illustrated in FIG. 4 is rigidly secured to the capstan about which it terminates in the articulation. In FIG. 4, the driving elements are not rigidly secured to any other element of the instrument. In FIG. 4, driving element pair E1, E2 is a single elongate loop which is rigidly fixed to capstan 202. This loop is fixed to capstan 202 at the point on capstan 202 which is most distal to the driving mechanism 300 and lies on the longitudinal axis of the shaft when the end effector, articulation and shaft are in the straight configuration shown in FIG. 4. Similarly, in FIG. 4, driving element pair E3, E4 is a single elongate loop which is rigidly fixed to capstan 203. This loop is fixed to capstan 203 at the point on capstan 203 which is most distal to the driving mechanism 300 and lies on the longitudinal axis of the shaft when the end effector, articulation and shaft are in the straight configuration shown in FIG. 4.

In an alternative configuration, driving elements E1 and E2 may be disconnected at the articulation. In other words, driving elements E1 and E2 may not form a continuous element about the capstan 203. Instead, driving elements E1 and E2 may each individually terminate at capstan 203, to which they are individually secured. Driving elements E1 and E2 may also be disconnected at the pulley arrangement. In other words, driving elements E1 and E2 may not form a continuous element about the pulley 306. Instead, driving elements E1 and E2 may each individually terminate at pulley 306, to which they are individually secured.

Similarly, driving elements E3 and E4 may be disconnected at the articulation. In other words, driving elements E3 and E4 may not form a continuous element about the capstan 202. Instead, driving elements E3 and E4 may each individually terminate at capstan 202, to which they are individually secured. Driving elements E3 and E4 may also be disconnected at the pulley arrangement. In other words, driving elements E3 and E4 may not form a continuous element about the pulley 305. Instead, driving elements E3 and E4 may each individually terminate at pulley 305, to which they are individually secured.

FIGS. 3 and 4 illustrate an example of a driving mechanism including only four pulleys: pulleys 305 and 306 of the pulley arrangement and pulleys 311 and 312. Further pulleys may additionally be utilised in the instrument to engage with the driving elements. For example, further pulleys may be used to ease the driving elements around each other to prevent them from rubbing against each other. Further pulleys may be used to ease one or more of the driving elements around other obstacles in the interior of the instrument, for example suturing thread, an optical fibre, an endoscopic camera. Suitably, each driving element retains its motion substantially parallel to the longitudinal axis of the instrument shaft despite the additional pulleys.

It may be desirable for the driving mechanism to be located in a different orientation or location at the proximal end of the instrument shaft in order to utilise the space in the central interior area of the instrument shaft for other components. In this case, additional pulleys may be used compared to FIG. 3 to locate the driving mechanism in the alternative orientation/location. This alternative orientation/location may be such that the axis 310 connecting the centres of the pulleys in the pulley arrangement is no longer parallel to the longitudinal axis of the instrument shaft. The pulley drive causes the pulley arrangement to move in a linear direction parallel to the axis 310 connecting the centres of the pulleys in the pulley arrangement. However, this linear movement may no longer be parallel to the longitudinal axis of the instrument shaft. However, by means of the additional pulleys, the same motions of the driving elements in the shaft are achieved by driving the pulley drive and the first and second drives.

The two pulleys 305 and 306 of the pulley arrangement 304 of FIG. 3 are connected by arm 307. However, any suitable connecting means may be used instead of the arm 307, as long as that connecting means maintains the pulleys 305 and 306 at a fixed separation from each other.

FIG. 4 illustrates the driving mechanism of FIG. 3 driving an articulation 103 at the distal end of the instrument shaft 102. The driving mechanism of FIG. 3 may be used to drive other configurations of articulation at the distal end of an instrument shaft. The driving mechanism of FIG. 3 can drive any articulation which is driveable with two pairs of driving elements which are capable of transferring motion as described herein.

The apparatus described herein enables motion of two pairs of driving elements as described herein utilising only three drives, instead of the four drives shown in FIG. 2. This enables the instrument to be lighter weight, and frees up additional space inside the instrument shaft for other components, or alternatively enables a shaft with a narrower diameter to be used.

It will be appreciated that the driving mechanism described herein could be modified to include further driving elements to transfer drive to further joints of an articulation at the distal end of the instrument shaft.

The driving mechanism 300 of FIG. 3 is substantially planar. The pulleys 305 and 306 and arm 307 are located in parallel planes. Pulleys 311 and 312 are located transverse to the plane of pulley arrangement 304. This results in the driving elements E1, E2, E3 and E4 being aligned. In other words, driving elements E1, E2, E3 and E4 are parallel to each other.

Figure 5:
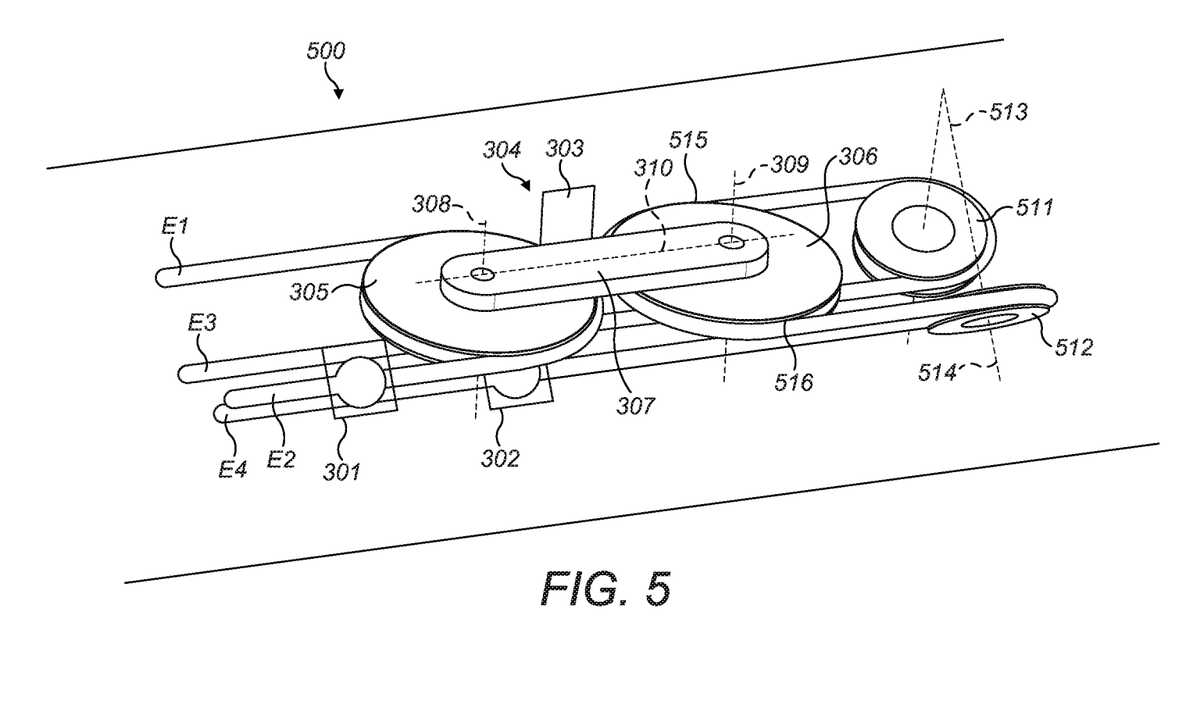
FIG. 5 illustrates a driving mechanism at the end of the surgical instrument distal from the end effector.

FIG. 5 illustrates a schematic drawing of a further exemplary driving mechanism 500 of the interior of a robotic surgical instrument at the end of the surgical instrument distal from the end effector. The driving mechanism 500 may be used to drive an articulation 103 at the distal end of the instrument shaft 102 as described above with respect to FIG. 4. The driving mechanism 500 of FIG. 5 is as described above with respect to the driving mechanism 300 of FIG. 3, except that the pulleys 511 and 512 have different orientations to the pulleys 311 and 312. Pulleys 511 and 512 are not mounted transverse to pulley arrangement 304. Pulley axis 513 of pulley 511 is not perpendicular to pulley axes 308 and 309 of pulleys 305 and 306. Pulley axis 514 of pulley 512 is not perpendicular to pulley axes 308 and 309 of pulleys 305 and 306. Pulleys 511 and 512 are not parallel to each other.

This results in the driving elements E1, E2, E3 and E4 not all being aligned with each other. In other words, driving elements E1, E2, E3 and E4 are not all parallel to each other as they extend towards a distal articulation. The angle of the pulleys 511, 512 may be so as to direct the driving elements E3, E4 towards the parts of the distal articulation of the instrument that they engage with. Causing the driving elements to be non-parallel provides additional space for locating the drives 301, 302, 303. This provides more engineering freedom in how the drives are designed.

The orientations of pulleys 311, 511 and pulleys 312, 512 are all such that they guide the driving elements E3, E4 onto the same pick up and take off points of the pulley 306. Both pulley 311 and pulley 511 guide the driving element E3 onto the same pick up point/take off point 515 of pulley 306. Both pulley 312 and pulley 512 guide the driving element E4 onto the same pick up point/take off point 516 of pulley 306.

Other component parts of the pulley arrangement of FIG. 3 may be in a different orientation to that shown in FIG. 3 or 5. For example, pulley 305 and pulley 306 may be non-parallel. Axes 308 and 309 may be non-parallel. As long as pulleys 305 and 306 move in unison with arm 307, axes 308 and 309 may be angled relative to each other.

The instrument could be used for non-surgical purposes. For example it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:
1. A robotic surgical instrument comprising:
   a shaft;
   an articulation attached to the distal end of the shaft, the articulation comprising a plurality of joints configured to articulate an end effector, the plurality of joints driveable by at least first and second pairs of driving elements; and
   a driving mechanism at the proximal end of the shaft, the driving mechanism comprising:
     a pulley arrangement comprising first and second pulleys attached together such that their separation is fixed, wherein the first pair of driving elements is constrained to move around the first pulley, and the second pair of driving elements is constrained to move around the second pulley; and a pulley drive configured to linearly displace the pulley arrangement, such that a linear displacement in a direction away from the distal end of the shaft causes the first pair of driving elements to be tensioned and the second pair of driving elements to be de-tensioned, and a linear displacement in an opposing direction towards the distal end of the shaft causes the second pair of driving elements to be tensioned and the first pair of driving elements to be de-tensioned.

2. A robotic surgical instrument as claimed in claim 1, wherein the pulley drive is configured to linearly displace the pulley arrangement such that a linear displacement in the direction away from the distal end of the shaft causes the first pair of driving elements to be tensioned and the second pair of driving elements to be compressed, and a linear displacement in the opposing direction towards the distal end of the shaft causes the second pair of driving elements to be tensioned and the first pair of driving elements to be compressed.

3. A robotic surgical instrument as claimed in claim 1, wherein the articulation is a wrist articulation and one of the plurality of joints is a pitch joint configured to pitch the wrist articulation, the first and second pairs of driving elements being connected to the wrist articulation such that when the pulley drive linearly displaces the pulley arrangement in the direction away from the distal end of the shaft the wrist articulation pitches in one direction about the pitch joint, and when the pulley drive linearly displaces the pulley arrangement in the opposing direction towards the distal end of the shaft the wrist articulation pitches in an opposing direction about the pitch joint.

4. A robotic surgical instrument as claimed in claim 1, wherein the pulley drive is configured to linearly displace the pulley arrangement in a direction parallel to the longitudinal axis of the shaft.

5. A robotic surgical instrument as claimed in claim 1, wherein at the proximal end of the shaft, the first pair of driving elements is constrained to move around the first pulley only with no further intervening pulleys, such that when the pulley drive linearly displaces the pulley arrangement away from the distal end of the shaft, the first pair of driving elements is tensioned.

6. A robotic surgical instrument as claimed in claim 1, wherein the second pair of driving elements is further constrained to move around third and fourth pulleys, the third and fourth pulleys being located further from the articulation than the pulley arrangement, wherein the second pair of driving elements extends from the articulation through the shaft, around the third and fourth pulleys to the second pulley, such that when the pulley drive linearly displaces the pulley arrangement towards the distal end of the shaft, the second pair of driving elements is tensioned.

7. A robotic surgical instrument as claimed in claim 1, the driving mechanism further comprising a first drive configured to drive the first pair of driving elements, such that a drive applied in one direction causes a first one of the first pair of driving elements to be tensioned and a second one of the first pair of driving elements to be compressed, and a drive applied in an opposing direction causes the first one of the first pair of driving elements to be compressed and the second one of the first pair of driving elements to be tensioned.

8. A robotic surgical instrument as claimed in claim 7, wherein one of the plurality of joints is configured to actuate opposing first and second jaws of an end effector, the first pair of driving elements being connected to the articulation such that when the first drive applies a drive in one direction the first jaw rotates in one direction about that joint, and when the first drive applies a drive in an opposing direction the first jaw rotates in an opposing direction about that joint.

9. A robotic surgical instrument as claimed in claim 7, wherein the first drive is a linear drive.

10. A robotic surgical instrument as claimed in claim 1, the driving mechanism further comprising a second drive configured to drive the second pair of driving elements, such that a drive applied in one direction causes a first one of the second pair of driving elements to be tensioned and a second one of the second pair of driving elements to be compressed, and a drive applied in an opposing direction causes the first one of the second pair of driving elements to be compressed and the second one of the second pair of driving elements to be tensioned.

11. A robotic surgical instrument as claimed in claim 10, wherein one of the plurality of joints is configured to actuate opposing first and second jaws of an end effector, the second pair of driving elements being connected to the articulation such that when the second drive applies a drive in one direction the second jaw rotates in one direction about that joint, and when the second drive applies a drive in an opposing direction the second jaw rotates in an opposing direction about that joint.

12. A robotic surgical instrument as claimed in claim 10, wherein the second drive is a linear drive.

13. A robotic surgical instrument as claimed in claim 1, wherein the driving elements are elongate and flexible.

14. A robotic surgical instrument as claimed in claim 1, wherein the driving elements are cables.

15. A robotic surgical instrument as claimed in claim 1, wherein the driving elements resist compression and tension forces.

16. A robotic surgical instrument as claimed in claim 1, wherein each pair of driving elements is formed of opposed portions of a single elongate element secured to one of the plurality of joints of the articulation.

17. A robotic surgical instrument as claimed in claim 1, wherein each driving element of the first pair of driving elements is formed of a distinct elongate element secured to one of the plurality of joints of the articulation and secured to the first pulley.

18. A robotic surgical instrument as claimed in claim 1, wherein each driving element of the second pair of driving elements is formed of a distinct elongate element secured to one of the plurality of joints of the articulation and secured to the second pulley.

* * * * *